United States Patent
Maniar

(10) Patent No.: US 10,576,047 B2
(45) Date of Patent: *Mar. 3, 2020

(54) FORMULATIONS FOR THE TREATMENT OF PAIN

(71) Applicant: Grünenthal GmbH, Aachen (DE)

(72) Inventor: Manoj Maniar, Fremont, CA (US)

(73) Assignee: Grünenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/999,705

(22) Filed: Aug. 20, 2018

(65) Prior Publication Data

US 2019/0247336 A1 Aug. 15, 2019

Related U.S. Application Data

(63) Continuation of application No. 14/517,603, filed on Oct. 17, 2014, now abandoned, which is a continuation of application No. 13/232,905, filed on Sep. 14, 2011, now Pat. No. 8,889,736, which is a continuation of application No. 11/145,266, filed on Jun. 2, 2005, now abandoned.

(60) Provisional application No. 60/576,372, filed on Jun. 2, 2004.

(51) Int. Cl.
| | |
|---|---|
| *A61K 31/165* | (2006.01) |
| *A61K 31/045* | (2006.01) |
| *A61K 31/16* | (2006.01) |
| *A61K 31/167* | (2006.01) |
| *A61K 31/17* | (2006.01) |
| *A61K 31/18* | (2006.01) |
| *A61K 31/24* | (2006.01) |
| *A61K 31/245* | (2006.01) |
| *A61K 31/325* | (2006.01) |
| *A61K 45/06* | (2006.01) |
| *A61K 9/00* | (2006.01) |

(52) U.S. Cl.
CPC .......... *A61K 31/165* (2013.01); *A61K 9/0019* (2013.01); *A61K 31/045* (2013.01); *A61K 31/16* (2013.01); *A61K 31/167* (2013.01); *A61K 31/17* (2013.01); *A61K 31/18* (2013.01); *A61K 31/24* (2013.01); *A61K 31/245* (2013.01); *A61K 31/325* (2013.01); *A61K 45/06* (2013.01)

(58) Field of Classification Search
CPC .... A61K 31/165; A61K 31/045; A61K 31/16; A61K 31/167; A61K 31/17; A61K 31/18; A61K 31/245; A61K 31/325; A61K 45/06; A61K 9/0019; A61K 31/24
See application file for complete search history.

(56) References Cited

U.S. PATENT DOCUMENTS

| | | | |
|---|---|---|---|
| 4,313,958 A | 2/1982 | LaHann | |
| 4,529,601 A | 7/1985 | Broberg et al. | |
| 4,701,471 A * | 10/1987 | Loucks, Sr. ............ | A61K 8/361 |
| | | | 514/784 |
| 4,812,446 A | 3/1989 | Brand | |
| 4,997,853 A | 3/1991 | Bernstein | |
| 5,134,166 A | 7/1992 | Bernstein | |
| 5,869,533 A | 2/1999 | Holt | |
| 5,962,532 A | 10/1999 | Campbell et al. | |
| 5,993,836 A * | 11/1999 | Castillo ............... | A61K 9/0014 |
| | | | 424/401 |
| 6,239,180 B1 * | 5/2001 | Robbins ............... | A61K 9/7023 |
| | | | 514/627 |
| 6,248,788 B1 | 6/2001 | Robbins et al. | |
| 6,277,398 B1 * | 8/2001 | Caruso ................. | A61K 9/7023 |
| | | | 424/443 |
| 6,297,290 B2 | 10/2001 | Guise et al. | |
| 6,299,902 B1 | 10/2001 | Jun et al. | |
| 6,368,618 B1 | 4/2002 | Jun et al. | |
| 6,410,036 B1 | 6/2002 | De Rosa et al. | |
| 6,841,161 B1 * | 1/2005 | Passmore ............... | A61K 9/107 |
| | | | 424/400 |
| 8,889,736 B2 | 11/2014 | Maniar | |
| 2003/0157138 A1 | 8/2003 | Eini et al. | |
| 2006/0100272 A1 | 5/2006 | Maniar | |
| 2012/0238624 A1 | 9/2012 | Maniar | |
| 2015/0250745 A1 | 9/2015 | Maniar | |

FOREIGN PATENT DOCUMENTS

| | | |
|---|---|---|
| EP | 1 201 241 A2 | 5/2002 |
| JP | H03-184915 A | 8/1991 |
| JP | 2001-213772 A | 8/2001 |
| JP | 2001-515492 A | 9/2001 |
| JP | 2002-29993 A | 1/2002 |
| JP | 2002-504523 A | 2/2002 |
| JP | 2003-512323 A | 4/2003 |
| JP | 2003-528821 A | 9/2003 |
| JP | 2004-500360 A | 1/2004 |
| WO | WO-90/14083 A1 | 11/1990 |
| WO | WO-98/40070 A1 | 9/1998 |
| WO | WO-98/51283 A1 | 11/1998 |
| WO | WO-99/43354 A2 | 9/1999 |
| WO | WO-99/43354 A3 | 9/1999 |
| WO | WO-01/28552 A2 | 4/2001 |
| WO | WO-01/28552 A3 | 4/2001 |
| WO | WO-01/43775 A2 | 6/2001 |
| WO | WO-01/43775 A3 | 6/2001 |

OTHER PUBLICATIONS

Epstein, J.B. et al. (Feb. 1994). "Topical Application of Capsaicin for Treatment of Oral Neuropathic Pain and Trigeminal Neuralgia," *Oral Surgery, Oral Medicine, Oral Pathology* 77(2):135-140.

Green, B.G. et al. (Mar. 2000). "Menthol Desensitization of Capsaicin Irritation: Evidence of a Short-Term Anti-Nociceptive Effect," *Physiol. Behavior*, 68(5):631-639.

(Continued)

*Primary Examiner* — Snigdha Maewall

(74) *Attorney, Agent, or Firm* — Morrison & Foerster LLP

(57) ABSTRACT

Formulations and methods are provided for the treatment of pain, and neuropathic pain in particular. The formulations are eutectic mixtures of a capsaicinoid and a local anesthetic agent and/or an anti-pruritic agent.

13 Claims, No Drawings

(56) References Cited

OTHER PUBLICATIONS

International Search Report dated Nov. 4, 2005, for PCT Patent Application No. PCT/US2005/019687, filed on Jun. 2, 2005, 3 pages.
Robbins, W.R. et al. (1998). "Treatment of Intractable Pain with Topical Large-Dose Capsaicin: Preliminary Report," *Anesthesia Analg.* 86:579-583.
Velvachol Cream, MSDS No. HP R-0141, Healthpoint, Ltd., Forth Worth, TX, Jul. 15, 2008, 3 pages.
Written Opinion of the International Searching Authority dated Nov. 4, 2005, for PCT Patent Application No. PCT/US2005/019687, filed on Jun. 2, 2005, 6 pages.
Yaksh, T.L. et al. (May 29, 1979). "Intrathecal Capsaicin Depletes Substance P in the Rat Spinal Cord and Produces Prolonged Thermal Analgesia," *Science* 206:481-483.

\* cited by examiner

FORMULATIONS FOR THE TREATMENT OF PAIN

CROSS-REFERENCE TO RELATED APPLICATIONS

This application is a continuation of U.S. patent application Ser. No. 14/517,603, filed Oct. 17, 2014, which is a continuation of U.S. patent application Ser. No. 13/232,905, filed Sep. 14, 2011, now U.S. Pat. No. 8,889,736, issued Nov. 18, 2014, which is a continuation application of U.S. application Ser. No. 11/145,266, filed Jun. 2, 2005, which claims priority under 35 U.S.C. § 119(e)(1) to provisional U.S. App. Ser. No. 60/576,372, filed Jun. 2, 2004, the disclosures of each of which are incorporated by reference herein in their entireties.

TECHNICAL FIELD

This invention relates generally to the management of pain, and more particularly relates to methods and compositions for the treatment of pain using a eutectic mixture of a capsaicinoid analgesic and a second drug that mitigates the side effects associated therewith.

BACKGROUND

Pain is a significant and costly healthcare problem, and is the most common reason patients seek medical care. Pain may be acute or chronic. Examples of acute pain include post-surgical pain and pain due to traumatic injuries. Chronic pain is generally more difficult to treat, and can be associated with any number of causes. For example, chronic pain may be associated with the inflammation of joints, tendons, nerves, muscle, and other soft tissues, with diseases such as cancer, or with injuries to the nervous system ("neuropathic" pain).

There is particular interest in developing improved therapies for the treatment of neuropathic pain, which is a challenging medical condition to treat as it can involve both the peripheral and central nervous systems. Neuropathic pain often persists following viral infection, trauma, administration of certain medications, or a metabolic insult. Nerves that remain intact following such as disease or injury can become hyperactive, causing pain even in the absence of a direct stimulus. Neuropathic pain is often described as a burning, excruciating pain and may never resolve. The severity of the pain is in part due to the nerve endings near the surface of the skin. Unfortunately, neuropathic pain is generally insensitive to administration nonsteroidal anti-inflammatory drugs, which are often successfully prescribed for the treatment of acute pain.

There are several types of neuropathic pain. The more common types include post-herpetic neuralgia, neuropathic pain related to human immunodeficiency virus (HIV)-associated neuropathy, neuropathic pain associated with diabetic neuropathy, and trigeminal neuralgia. Post-herpetic neuralgia is chronic, mild to severe burning pain on the surface of the skin that develops in some patients after healing of shingles (herpes zoster). Both the HIV infection, as well as HIV medications, are associated with the development of neuropathy and neuropathic pain. This pain typically affects the feet and hands, and is commonly referred to as neuropathic pain related to HIV-associated neuropathy. Diabetic neuropathy is a common complication of diabetes mellitus, and can lead to amputation. Peripheral diabetic neuropathy is typically characterized by pain, weakness, and reduced or lost sensation in the feet. Trigeminal neuralgia is a disorder of the trigeminal nerve, which causes episodes of intense, stabbing, electric shock-like pain in the areas of the face in which nerve endings are located (e.g., the lips, eyes, nose, scalp, forehead, upper jaw, and lower jaw). Other types of diabetic neuropathy include autonomic neuropathy, proximal neuropathy, and focal neuropathy.

In addition to these common types of neuropathic pain, there are numerous medical conditions that are associated with neuropathic pain. These include traumatic nerve injury, stroke, multiple sclerosis, epilepsy, spinal cord injury, and cancer.

Current therapies for neuropathic pain are limited, often involving the administration of multiple medications with the understanding that pain relief will not be complete and the quality of life may not be restored. These therapies may require frequent dosing, can be associated with undesirable systemic side effects, and typically provide unsatisfactory relief. Therefore, there remains a need for a therapeutic option developed specifically for neuropathic pain that provides sustained relief while minimizing the potential for systemic side effects and drug-drug interactions.

Capsaicin (8-methyl-N-vanillyl-6Z-nonenamide) and "synthetic" capsaicin (N-vanillyl-nonenamide) are disclosed as analgesics in U.S. Pat. No. 4,313,958 to LaHann. Analgesic activity of capsaicin has also been discussed in the chemical and medical literature, including Yaksh, et al. (1979) Science 206:481-483. Capsaicin is derived from the plants of the solanaceae family, and is the purified extracted alkaloid from red chili peppers. Capsaicin has been found to relieve pain by reducing substance P, which is found at nerve endings and is involved in transmitting neuralgic and arthritic pain signals to the brain. Pain relief is not instantaneous after application as it is the cumulative depletion of substance P over a period of weeks that brings the full effect.

Low-concentration capsaicin topical creams have been used for years to treat neuropathic pain, but their use has been limited because they are inconvenient to apply and must be applied at regular intervals throughout the day, even then achieving only modest pain relief at best. Unfortunately, capsaicin is a potent skin irritant, and the application of capsaicin itself can cause burning pain and hyperalgesia, exacerbating the pain being treated. This intense initial burning effect usually diminishes after the first few days of application and in most cases disappears with time and continued use; the initial side effects are sufficiently severe, however, to significantly impact on patient compliance, thus diminishing the overall therapeutic value of capsaicin as an effective treatment for pain.

In order to minimize the initial burning sensation associated with the topical administration of capsaicin formulations, the skin can be pre-treated with an anesthetic agent. Two-step therapy can be cumbersome for chronic users, however. Furthermore, because capsaicin is poorly soluble in aqueous solvents, any capsaicin formulation used in this context will have a relatively low concentration of the drug, again requiring frequent application as noted above.

Several patents describe topical capsaicin formulations and are of background interest with respect to the present invention: U.S. Pat. No. 4,812,446 to Brand describes an analgesic composition comprising capsaicin or a capsaicin analogue and an analgesic selected from the class of non-steroidal anti-inflammatory, antipyretic and analgesic drugs. U.S. Pat. No. 4,997,853 to Bernstein describes a 0.01-1.0 wt % capsaicin formulation containing 0.5-25 wt % of a topical anesthetic. U.S. Pat. No. 5,962,532 to Campbell et al. describes the use of a 0.01-10 wt % capsaicin formulation to treat pain. Anesthesia is first provided to the site where the capsaicin is to be administered, for example, by epidural regional anesthesia. U.S. Pat. No. 6,248,788 to Robbins et al. describes a 5-10 wt % capsaicin formulation, accompanied by a regional anesthetic, preferably by means of a somatic or neuraxial block. See also, Robbins et al. (1998) *Anesth. Analg.* 86:579-583. U.S. Pat. No. 5,869,533 to Holt describes a polymeric formulation of 0.00125-1 wt % capsaicin together with a plant extract to neutralize the discomfort resulting from the application of capsaicin. Although directed towards providing improved anesthesia instead of pain relief, U.S. Pat. No. 6,299,902 to Jun et al. describes a two-phase liquid composition comprising a local anesthetic agent, a first melting point depressing agent, for example capsaicin, and a second melting point depressing agent, which is a liquid, more specifically an alcohol.

Despite the advancements in the art, there remains a need for more effective pain-relieving formulations. An ideal formulation, particularly for the treatment of neuropathic pain, would contain higher levels of capsaicin than previously possible but not cause the discomfort and burning associated with capsaicin formulations of the prior art.

SUMMARY OF THE INVENTION

The present invention is directed to the aforementioned need in the art, and provides novel compositions and methods for the treatment of pain, including but not limited to neuropathic pain.

In one embodiment, the invention provides a therapeutic formulation for the treatment of pain wherein the formulation comprises a substantially nonaqueous binary eutectic mixture of active agents that are both solid at 25° C. The first active agent is a capsaicinoid having the structure of formula (I)

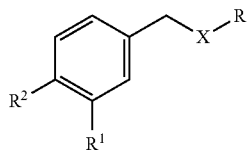

wherein $R^1$ is hydrogen, hydroxyl or methoxy, $R^2$ is hydroxyl or $C_2$-$C_6$ alkoxycarbonyl, X is selected from

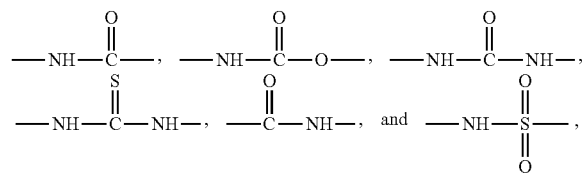

and R is selected from $C_5$-$C_{11}$ alkyl, $C_5$-$C_{11}$ alkenyl, $C_{11}$-$C_{23}$ cis-alkenyl, $C_{11}$-$C_{23}$ alkynyl, and $C_{11}$-$C_{23}$ alkadienyl. The second active agent is one that is effective to decrease at least one side effect associated with capsaicin monotherapy, and may be a local anesthetic agent or an anti-pruritic agent.

In another embodiment, a therapeutic formulation for the treatment of pain is provided that comprises a substantially nonaqueous ternary eutectic mixture of active agents that are all solid at 25° C. The first active agent is a capsaicinoid, the second active agent is a local anesthetic agent, and the third active agent is an anti-pruritic agent.

In a further embodiment, a method is provided for treating a patient suffering from pain by administering a therapeutically effective amount of a formulation of the invention to the patient. The pain may be neuropathic pain, as may be associated with HIV or diabetic neuropathy.

DETAILED DESCRIPTION OF THE PREFERRED EMBODIMENTS

Unless otherwise indicated, the invention is not limited to specific active agents, pharmaceutical formulations, modes of administration, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "an active agent" encompasses a combination or mixture of different active agents as well as a single active agent, and the like. In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. If not otherwise indicated, the term "alkyl" includes linear, branched, cyclic, unsubstituted, substituted, and/or heteroatom-containing alkyl.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. If not otherwise indicated, the term "alkenyl" includes linear, branched, cyclic, unsubstituted, substituted, and/or heteroatom-containing alkenyl.

The term "alkynyl" as used herein refers to a linear or branched hydrocarbon group of 2 to 24 carbon atoms containing at least one triple bond, such as ethynyl, n-propynyl, and the like. If not otherwise indicated, the term "alkynyl" includes linear, branched, cyclic, unsubstituted, substituted, and/or heteroatom-containing alkynyl.

When referring to an active agent, applicants intend the term to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

The terms "treating" and "treatment" as used herein refer to reduction in severity and/or frequency of pain, elimination of pain, prevention of pain, and/or prevention of pain.

By the terms "effective amount" and "therapeutically effective amount" of a formulation of the invention is meant a nontoxic but sufficient amount of the formulation to provide the desired effect. The amount that is "effective" will vary from subject to subject, depending on the age and general condition of the individual, the particular active agents, and the like. Thus, it is not always possible to specify an exact "effective amount." However, an appropriate "effective" amount in any individual case may be determined by one of ordinary skill in the art using routine experimentation. For example, a therapeutically effective amount of capsaicin is that quantity needed to treat or prevent pain, e.g., neuropathic pain. A therapeutically effective amount of an anesthetic agent is that concentration needed to prevent burning or discomfort from capsaicin at the site of administration.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing of that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

Accordingly, in a first embodiment, a therapeutic formulation is provided that is substantially nonaqueous, i.e., contains less than 5 wt. %, preferably less than 2.5 wt. %, and most preferably less than 1 wt. % water, and is composed of a binary eutectic mixture of a capsaicinoid and a second active agent. The term "binary eutectic mixture" refers to a mixture of two components that has a melting point that lower than the melting point of either component. In the present context, the two components of the binary eutectic mixture are solid at 25° C. but the eutectic mixture itself is preferably a liquid at 25° C. The term "capsaicinoid" refers to an analgesic agent, generally used as a topical analgesic agent, having the structure of formula (I)

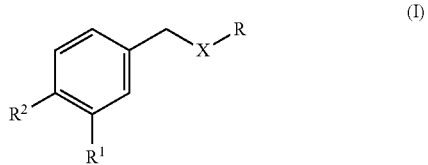

(I)

wherein $R^1$ is hydrogen, hydroxyl or methoxy, $R^2$ is hydroxyl or $C_2$-$C_6$ alkoxycarbonyl, X is selected from

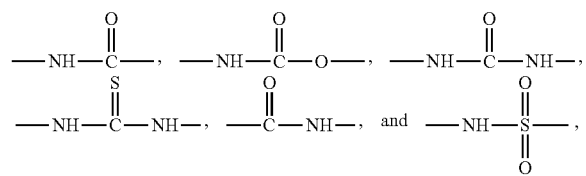

and R is selected from $C_5$-$C_{11}$ alkyl, $C_5$-$C_{11}$ alkenyl, $C_{11}$-$C_{23}$ cis-alkenyl, $C_{11}$-$C_{23}$ alkynyl, and $C_{11}$-$C_{23}$ alkadienyl.

Generally, the capsaicinoid is selected from resiniferatoxin, N-vanillyl-alkadienamides, N-vanillyl-alkanedienyls, N-vanillyl-monounsaturated alkenamides, N-vanillylsulfonamides, and hydroxyphenylacetamides. In a preferred embodiment, the capsaicinoid is an N-vanillyl-monounsaturated alkenamide (i.e., $R^1$ is methoxy, $R^2$ is hydroxyl, X is —NH—(CO)—, and R is an alkene chain), and in a particularly preferred embodiment, the N-vanillyl-monounsaturated alkenamide is capsaicin (R is —$(CH_2)_4$—CH=CH—CH$(CH_3)_2$).

The second active agent may be a local anesthetic agent that can alleviate the pain and discomfort associated with capsaicin monotherapy (i.e., administration of capsaicin without a second active agent) or may be an anti-pruritic agent, which can alleviate the itching and irritation associated with administration of capsaicin. Any local anesthetic agent or anti-pruritic agent that is a solid at 25° C. can be used in the formulations of the invention. The term "solid" is intended to include hygroscopic compounds and other solids that, under certain conditions, take a semisolid form.

The local anesthetic agent is a drug that provides local numbness or pain relief by producing a reversible loss of sensation by inhibiting or by decreasing pain at the site of application, without resulting in a loss of nerve control. Representative local anesthetic agents include amylocaine, articaine, benzocaine, bupivacaine, butacaine, 2-chloroprocaine, cinchocaine, dexivacaine, diamocaine, dibucaine, etidocaine, ketocaine, lidocaine, mepivacaine, oxybuprocaine, parethoxycaine, prilocaine, procaine, propanocaine, proparacaine, propoxycaine, pyrrocaine, risocaine, rodocaine, ropivacaine, tetracaine, and combinations thereof. Preferred local anesthetic agents for use in the present formulations are lidocaine and tetracaine.

Exemplary anti-pruritic agents include, by way of illustration and not limitation, camphor, phenol, and menthol.

The active agents may be incorporated into the formulation in the form of a salt, ester, amide, prodrug, active metabolite, analog, or the like, provided that the salt, ester, amide, prodrug, active metabolite, or analog is pharmaceutically acceptable and pharmacologically active in the present context. Salts, esters, amides, prodrugs, active metabolites, analogs, and other derivatives of the active agents may be prepared using standard procedures known to those skilled in the art of synthetic organic chemistry and described, for example, by J. March, *Advanced Organic Chemistry: Reactions, Mechanisms and Structure,* 4th Ed. (New York: Wiley-Interscience, 1992). In a preferred embodiment, however, the free base form of the local anesthetic agent is used since, typically, the free base form has a lower melting point than the equivalent salt.

The binary eutectic mixture enables incorporation of the capsaicinoid into the formulation at higher levels than previously possible. In the aforementioned formulations, the capsaicinoid represents about 10 wt. % to about 70 wt. % of the formulation, preferably about 40 wt. % to about 70 wt. % of the formulation. Ideally, the formulation is substantially free of components other than the two active agents (i.e., the active agents represent at least 90 wt. % of the formulation, preferably at least 95 wt. % of the formulation, and optimally at least 99 wt. % of the formulation), and therefore does not contain carriers, excipients, enhancers, or other additives. Pharmaceutically acceptable carriers can, however, be included if desired, and the invention thus encompasses those embodiments wherein the capsaicin and secondary agents are admixed with one or more pharmaceutically acceptable carriers suited to the particular type of formulation, i.e., solution, gel, cream, lotion, ointment, suppository, or the like.

In another embodiment, a therapeutic formulation is provided that is composed of a capsaicinoid having the structure of formula (I) and two additional active agents, wherein the formulation is substantially nonaqueous as defined above. Each of the two additional active agents is effective to decrease at least one side effect associated with capsaicin monotherapy, e.g., pain, discomfort, itching, or irritation. In a preferred embodiment, one of the additional active agents is a local anesthetic agent as described above, and the other of the additional active agents is an anti-pruritic agent as also described above. Preferred capsaicinoids are N-vanillyl-monounsaturated alkenamides, with capsaicin per se particularly preferred.

In the ternary eutectic mixture, the capsaicinoid generally, although not necessarily, represents about 10 wt. % to about 50 wt. % of the formulation, with the two active agents together representing about 50 wt. % to about 90 wt. % of the formulation. In a particularly preferred embodiment, the weight ratio of the two additional active agents, e.g., the local anesthetic agent and the anti-pruritic agent, is approximately 1:1. Thus, in the latter case, the three active agents, the capsaicinoid, the local anesthetic agent, and the anti-pruritic agent, will be in an approximately 10:45:45 to 50:25:25 ratio by weight.

To prepare the formulations of the invention, the solid components are mixed together. After about 30 minutes, a moist mixture is formed, and subsequently, for example over a 24-hour period, a liquid is formed and the ingredients remain in the liquid state. The mixture may be warmed to expedite formation of the liquid, although this is not required.

Because the formulations of the invention are primarily or even entirely composed of active agents, and furthermore because the capsaicinoid represents a substantial fraction of the formulation, extremely high doses of the capsaicinoid can be delivered with a relatively small amount of the formulation. The incorporation of the additional active agents, e.g., the local anesthetic agent and/or the anti-pruritic agent, will facilitate patient compliance since the side effects of capsaicin are substantially reduced. In addition, there is no need to further formulate the capsaicin into cream or gel because the liquid can be packaged as is, for example, in a "roll-on" type applicator.

The formulations of the invention find utility in pain caused by inflammation of joints, tendons, nerves, muscle, and other soft tissues, including arthritic pain; back pain; headache pain; pain caused by cancer; and neuropathic pain, the latter of which is of particular interest. Examples of neuropathic pain, for which the formulations of the invention are particularly well-suited, include, post-herpetic neuralgia, neuropathic pain related to HIV-associated neuropathy, pain associated with diabetic neuropathy, and neuropathic pain associated with trigeminal neuralgia.

Administration of a formulation of the invention may be carried out using any appropriate mode of administration. Typically, administration will be carried out topically rather than systemically, although systemic administration, generally parenteral administration, is possible.

It is to be understood that while the invention has been described in conjunction with the preferred specific embodiments thereof, that the foregoing description as well as the examples that follow, are intended to illustrate and not limit the scope of the invention. It should be understood by those skilled in the art that various changes may be made and equivalents may be substituted without departing from the scope of the invention, and further that other aspects, advantages and modifications will be apparent to those skilled in the art to which the invention pertains.

Example 1

Capsaicin ("Cap") and lidocaine ("Lido") were mixed in the various ratios set forth in Table 1. Some of the formulations spontaneously became partially liquid. All of the formulations were mildly heated to form a uniform solution. The solutions were allowed to crystallize and/or separate at room temperature. The mixtures were also analyzed by DSC.

TABLE 1

| Composition | Observations | | | |
|---|---|---|---|---|
| Cap:Lido | Immediately | 24 hours | Melt/48 hours | 96 hours |
| 100 | Solid | Solid | Solid | Solid |
| 90:10 | Solid | Wet mass | Wet mass | Wet mass |
| 80:20 | Solid | Wet mass | Wet mass | Wet mass |
| 70:30 | Wet mass | Wet mass | Liquid | Liquid |
| 60:40 | Wet mass | Wet mass | Liquid | Liquid |
| 50:50 | Wet mass | Wet mass | Liquid | Liquid |
| 40:60 | Wet mass | Wet mass | Liquid | Liquid |
| 30:70 | Solid | Wet mass | Wet mass | Wet mass |
| 20:80 | Solid | Wet mass | Wet mass | Wet mass |
| 10:90 | Solid | Wet mass | Wet mass | Wet mass |
| 0:100 | Solid | Solid | Solid | Solid |

Example 2

Capsaicin, menthol, and lidocaine were mixed in the ratios given in Table 2. As in Example 1, some of the formulations spontaneously became partially liquid. All of the formulations were mildly heated to form a uniform solution. The solutions were allowed to crystallize and/or separate at room temperature.

TABLE 2

| Composition | Observations | | |
|---|---|---|---|
| Cap:Menthol:Lido | Immediately | 24 hours | Melt/(over 2 weeks) |
| 100 | Solid | Solid | Solid |
| 10:45:45 | Solid | Wet mass | Liquid |
| 30:35:35 | Solid | Wet mass | Liquid |
| 40:30:30 | Wet mass | Wet mass | Liquid |
| 50:25:25 | Wet mass | Wet mass | Liquid |
| 60:20:20 | Wet mass | Wet mass | Wet mass |
| 70:15:15 | Wet mass | Wet mass | Wet mass |
| 90:5:5 | Wet mass | Wet mass | Wet mass |

Example 3

Capsaicin ("Cap") and tetracaine ("Tetra") were mixed in the ratios set forth in Table 3. As in Example 1, some of the formulations spontaneously became partially liquid. All of the formulations were mildly heated to form a uniform solution. The solutions were allowed to crystallize and/or separate at room temperature.

TABLE 3

| Composition | Observations | | |
|---|---|---|---|
| Cap:Tetra | Immediately | 24 hours | Melt/(over 2 weeks) |
| 100 | Solid | Solid | Solid |
| 10:90 | Solid | Wet mass | Liquid |
| 30:70 | Solid | Wet mass | Liquid |
| 40:60 | Wet mass | Wet mass | Liquid |
| 50:50 | Wet mass | Wet mass | Liquid |
| 60:40 | Wet mass | Wet mass | Wet mass |
| 70:30 | Wet mass | Wet mass | Wet mass |
| 90:10 | Wet mass | Wet mass | Wet mass |

Example 4

Capsaicin ("Cap") and menthol were mixed in the different ratios set forth in Table 4. Some of the formulations spontaneously became partially liquid. All of the formulations were mildly heated to form a uniform solution. The solutions were allowed to crystallize and/or separate at room temperature.

TABLE 4

| Composition | Observations | | | |
|---|---|---|---|---|
| Cap:Menthol | Immediately | 24 hours | Melt/(1 week) | Over 2 weeks |
| 100 | Solid | Solid | Solid | Solid |
| 10:90 | Solid | Wet mass | Wet mass | Wet mass |
| 30:70 | Solid | Wet mass | Wet mass | Wet mass |
| 40:60 | Wet mass | Wet mass | Liquid | Wet mass |
| 50:50 | Wet mass | Wet mass | Liquid | Wet mass |
| 60:40 | Wet mass | Wet mass | Liquid | Wet mass |
| 70:30 | Wet mass | Wet mass | Wet mass | Wet mass |
| 90:10 | Solid | Wet mass | Wet mass | Solid |

I claim:

1. A substantially nonaqueous therapeutic formulation comprising a binary eutectic mixture of:
   (a) a capsaicinoid having the structure of formula (I)

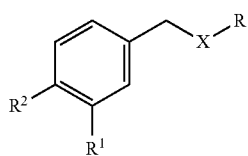

wherein $R^1$ is hydrogen, hydroxyl or methoxy, $R^2$ is hydroxyl or $C_2$-$C_6$ alkoxycarbonyl, X is selected from

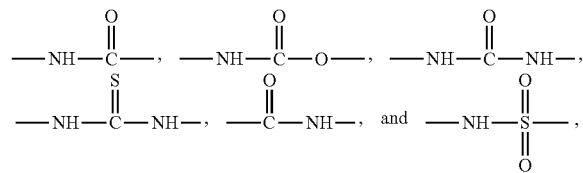

and R is selected from $C_5$-$C_{11}$ alkyl, $C_5$-$C_{11}$ alkenyl, $C_{11}$-$C_{23}$ cis-alkenyl, $C_{11}$-$C_{23}$ alkynyl, and $C_{11}$-$C_{23}$ alkadienyl, provided that the capsaicinoid is other than capsaicin, wherein the capsaicinoid represents about 10 wt. % to about 70 wt. % of the formulation; and (b) a second active agent effective to decrease at least one side effect associated with capsaicin monotherapy, said second agent existing as a solid at 25° C., and wherein said second agent is a local anesthetic agent selected from the group consisting of amylocaine, articaine, benzocaine, bupivacaine, butacaine, 2-chloroprocaine, cinchocaine, dexivacaine, diamocaine, dibucaine, etidocaine, ketocaine, lidocaine, mepivacaine, oxybuprocaine, parethoxycaine, prilocaine, procaine, propanocaine, proparacaine, propoxycaine, pyrrocaine, risocaine, rodocaine, ropivacaine, tetracaine, and combinations thereof; and
   wherein the formulation contains less than 5 wt. % water.

2. The formulation of claim 1, wherein the capsaicinoid is selected from resiniferatoxin, N-vanillyl-alkadienamides, N-vanillyl-alkanedienyls, N-vanillyl-monounsaturated alkenamides, N-vanillylsulfonamides, and hydroxyphenylacetamides.

3. The formulation of claim 2, wherein the capsaicinoid is an N-vanillyl monounsaturated alkenamide.

4. The formulation of claim 1, wherein the local anesthetic agent is lidocaine.

5. The formulation of claim 1, wherein the local anesthetic agent is tetracaine.

6. The formulation of claim 1, wherein the capsaicinoid represents about 40 wt. % to about 70 wt. % of the formulation.

7. A method for treating a patient suffering from pain, comprising administering to the patient a therapeutically effective amount of the formulation of claim 1.

8. The method of claim 7, wherein the formulation is administered topically.

9. The method of claim 8, wherein the pain is caused by inflammation of joints, tendons, nerves, or muscle.

10. The method of claim 7, wherein the pain is caused by cancer.

11. The method of claim 7, wherein the pain is neuropathic pain.

12. The formulation of claim 1, wherein the formulation contains less than 1 wt. % water.

13. The formulation of claim 1, wherein the formulation is substantially free of additional components other than the capsaicinoid and the local anesthetic agent.

* * * * *